United States Patent [19] [11] Patent Number: 5,024,616
Ogle, II                                 [45] Date of Patent: Jun. 18, 1991

[54] DISPOSABLE SHEATH FOR HYPODERMIC CANNULA USED WITH A SYRINGE

[75] Inventor: George Braddock Ogle, II, Alta Loma, Calif.

[73] Assignee: International Medication Systems, Limited, South El Monte, Calif.

[21] Appl. No.: 271,749

[22] Filed: Nov. 15, 1988

[51] Int. Cl.$^5$ ............................................. A61M 5/32
[52] U.S. Cl. ................................. 604/192; 604/198; 604/110; 128/918
[58] Field of Search ............... 604/198, 197, 192, 263, 604/110, 195; 128/763, 764, 765

[56] References Cited

U.S. PATENT DOCUMENTS

| | | | |
|---|---|---|---|
| 4,425,120 | 1/1984 | Sampson | 604/198 |
| 4,631,057 | 12/1986 | Mitchell | 604/198 |
| 4,702,739 | 10/1987 | Milorad | 604/198 |
| 4,801,295 | 1/1989 | Spencer | 604/198 |
| 4,816,022 | 3/1989 | Poncy | 604/198 |
| 4,826,490 | 5/1989 | Byrne et. al. | 604/198 |
| 4,840,619 | 6/1989 | Hughes | 604/187 |
| 4,842,587 | 6/1989 | Poncy | 604/198 |
| 4,846,796 | 7/1989 | Carrell et al. | 604/110 |
| 4,892,107 | 1/1990 | Haber | 128/763 |
| 4,897,083 | 1/1990 | Martell | 604/192 |
| 4,900,310 | 2/1990 | Ogle, II | 604/198 |

Primary Examiner—C. Fred Rosenbaum
Assistant Examiner—Mark O. Polutta
Attorney, Agent, or Firm—Christie, Parker & Hale

[57] ABSTRACT

A protective device for a removable cannula used with a hypodermic syringe includes an elongated sheath open at one end. A piston in the sheath is slidable longitudinally between an extended position and a retracted position. The removable cannula is on one side of the piston, and the hypodermic syringe on the outer side. Means are provided for connecting the cannula to the syringe through a bore in the piston so the piston is between the cannula and the syringe barrel. With the piston in the extended position, the cannula extends from one end of the sheath, and the hypodermic syringe plunger extends from the other end so the assembly is ready to use in the same manner as a conventional hypodermic syringe. After use, the piston is moved to the retracted position so that the scarf end of the cannula is safely enclosed within the sheath.

14 Claims, 3 Drawing Sheets

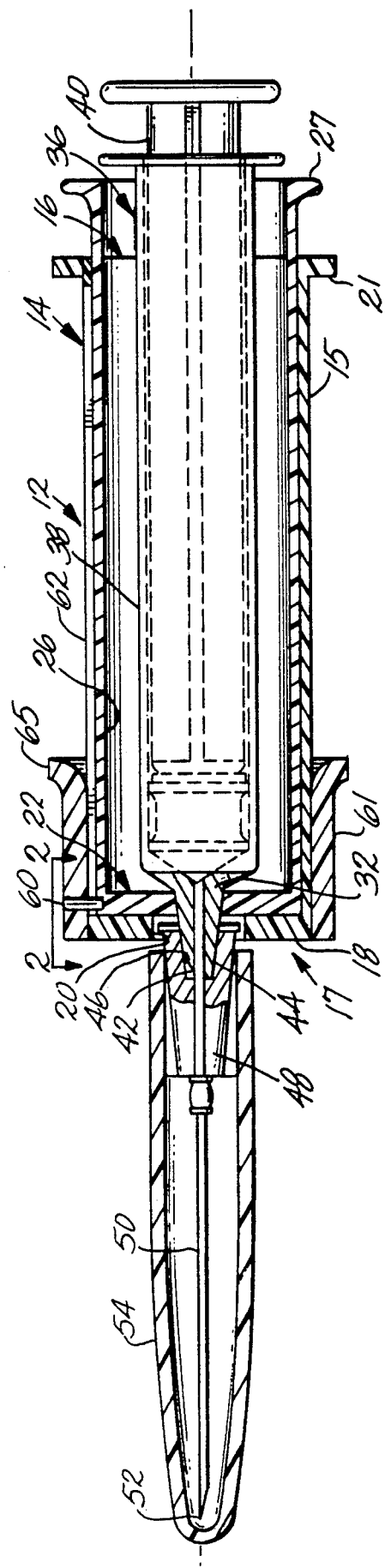

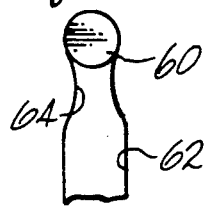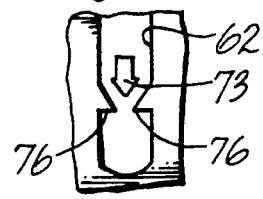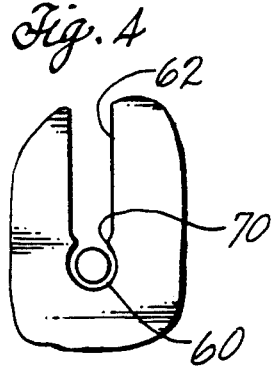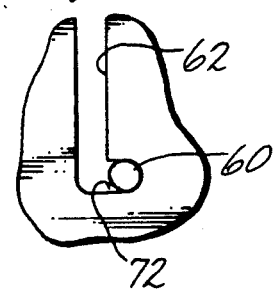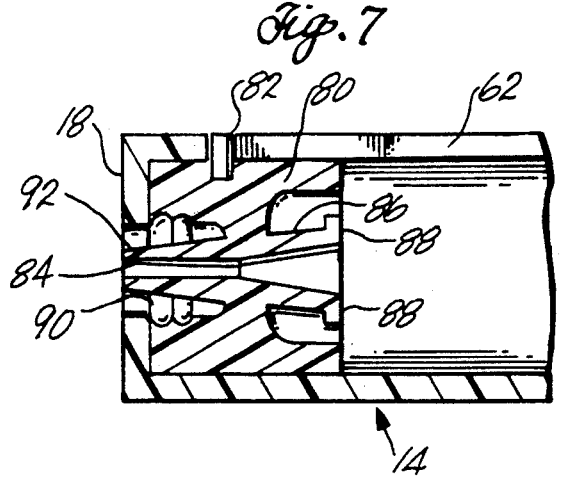

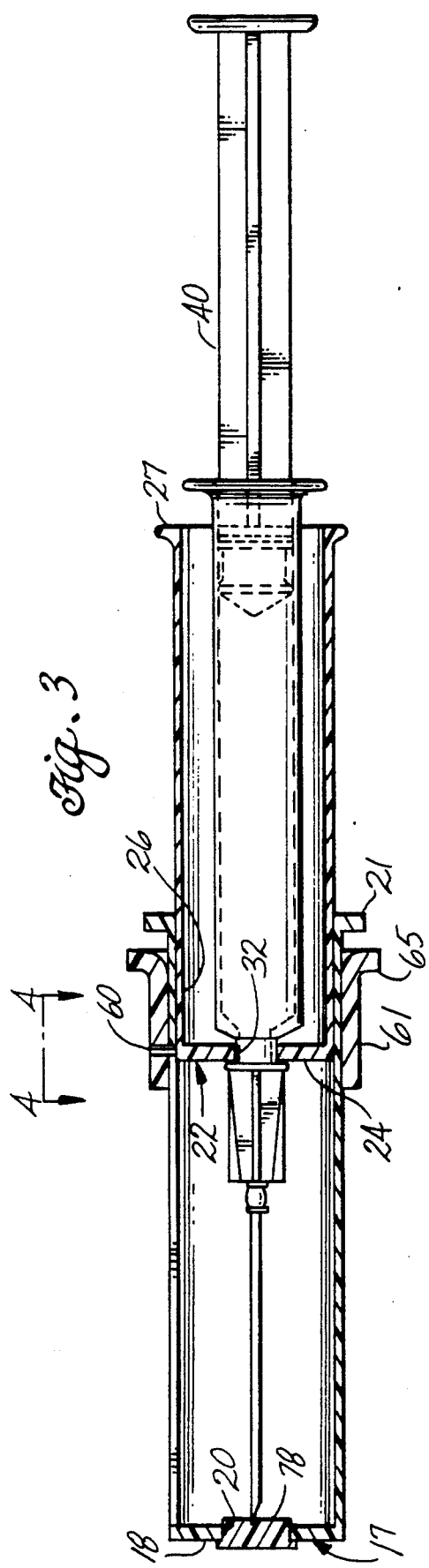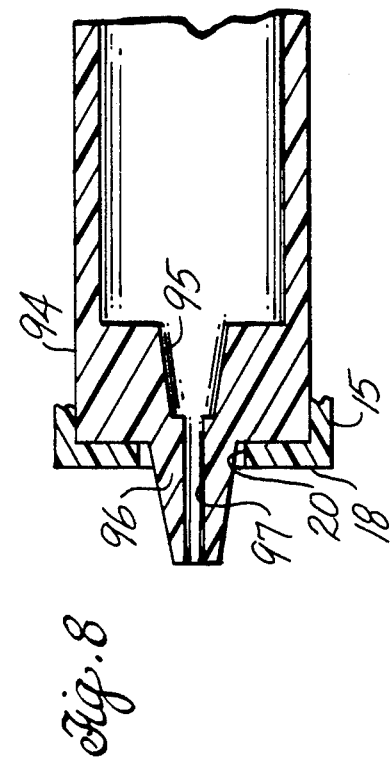

DISPOSABLE SHEATH FOR HYPODERMIC CANNULA USED WITH A SYRINGE

BACKGROUND OF THE INVENTION

Disposable hypodermic syringes are used in large quantities for administering medication to patients. After use, the syringes must be discarded safely to prevent accidental puncturing of hospital and other personnel with a contaminated cannula.

The conventional hypodermic syringe includes a barrel open at one end to receive a plunger, which, when operated, forces liquid in the barrel out the discharge end through an opening surrounded by a fitting adapted to be connected to a mating fitting on a hub carried by a cannula at a location remote from the scarf, or sharpened end, of the cannula. The cannula is supplied separately in a sterile package and with a protective cap that fits over the scarf end of the cannula and seats snugly on the hub, which carries the cannula fitting.

To use the cannula in the conventional way, it is attached to the barrel of a syringe with the protective cap still in place over the cannula. To load the syringe with medication, the cannula cap is removed and medication is drawn into the syringe barrel. Accidental puncturing during needle recapping at this time is not considered a great risk because the needle is sterile. If accidental puncture occurs, the assembly is discarded.

In prior art practice, once the medication is properly stored in a sterile syringe/cannula assembly, it is administered to the patient by removing the cannula cap and puncturing the patient's skin for either intravenous or intramuscular injection. The needle is then withdrawn from the patient. The used needle, which is still attached to the syringe, is recapped for proper disposal.

Recapping the cannula involves a substantial chance of accidental puncture with the contaminated cannula because the opening of the protective cap is small (about ¼" in diameter). The probability of accidental puncture is increased because the cap is held in one hand and the syringe in the other, and the hand holding the cap must make the same relative movement toward the scarf which is used to puncture the skin. If the tip of the cannula misses the opening of the cap, puncture of the fingers holding the cap can easily occur. In the past, such punctures were of concern because of hepatitis. With the onset of the acquired immune deficiency syndrome (AIDS), the puncture wound from a contaminated cannula exposes personnel to the risk of contracting AIDS, an even deadlier disease.

Many attempts have been made to solve the problem of accidental puncture by providing a protective sheath which covers the cannula after it is used. Examples of such attempts are shown in U.S. Pat. No. 4,702,738, issued Oct. 27, 1987, to Spencer; U.S. Pat. No. 4,737,144, issued Apr. 12, 1988, to Choksi; and U.S. Pat. No. 4,743,233, issued May 10, 1988, to Schneider. The disadvantage of these prior art sheaths is that they require specially-constructed syringes.

The present invention reduces the risk of accidental puncture with a contaminated cannula by providing a protective device which permits the cannula to be retracted into a sheath as the cannula is withdrawn from the patient, and without requiring relative movement of the hand in the direction which causes the cannula to puncture the skin. With the cannula in the retracted position, personnel are protected from inadvertent puncture by a contaminated cannula. In the preferred form of the invention, the device may be operated with only one hand to retract the cannula in the sheath, thereby minimizing the danger of accidental puncture with the cannula.

The protective sheath of this invention can be used with standard, mass-produced syringes and cannulas of different sizes, and without requiring any special construction of the standard syringe.

SUMMARY OF THE INVENTION

The protective device of this invention includes an elongated sheath open at a first end. A piston is disposed in the sheath to be longitudinally slidable relative to the sheath between an extended position and a retracted position. The piston has a longitudinal bore extending through it so that a removable cannula disposed on one side of the piston can be connected through the bore to the discharge end of a syringe barrel. In this way, the piston is secured between the removable cannula and the discharge end of the barrel. With the piston in the extended position, the scarf end of the cannula extends from a second end of the sheath, and the barrel plunger extends from the first or open end of the sheath, so the assembly can be used in the same manner as a conventional hypodermic syringe.

In one form of the invention, where the syringe barrel carries a tapered fitting at the discharge end to make a snug friction fit with a mating tapered fitting at the inlet end of the hub on the cannula, the piston is simply sandwiched between the cannula hub and the discharge end of the syringe barrel.

In another form, adapted to be used with a cannula and syringe barrel which have mating threaded fittings, the piston has a threaded fitting on one side to receive the syringe barrel threaded fitting, and has a second threaded fitting on the other side to receive the cannula hub threaded fitting. In this way, the piston is securely locked to the syringe barrel and the cannula, and a bore through the piston provides communication between the cannula and the barrel of the syringe.

In yet another form of the invention, the piston has a tapered socket on one side to receive the tapered plug at the discharge end of the syringe barrel, and a tapered plug on the other side to fit into the tapered socket at the inlet end of the hub.

Preferably, the piston carries a pin which extends laterally through a longitudinal slot in the sheath wall. Detent means are provided for locking the pin and piston in the retracted and extended positions. An exterior sleeve makes a close sliding fit around the outside of the sheath and is secured to the pin. An outwardly extending handle on the sleeve makes it possible to slide the sleeve longitudinally along the sheath with only one hand to carry the piston and cannula to the retracted position.

Preferably, the second end of the sheath includes an end wall which has a bore collinear with the bore through the piston, and a removable plug is included for closing that bore when the cannula is retracted within the sheath.

DESCRIPTION OF THE DRAWINGS

FIG. 1 is a sectional elevation of one of the presently preferred embodiments of the invention, showing the piston and cannula in the extended position and with a protective cap over the cannula;

FIG. 2 is a view taken on line 2—2 of FIG. 1, showing detent means for securing the piston and pin in the extended position within the sheath;

FIG. 3 is a sectional elevation of the device shown in FIG. 1, except that the piston and cannula (without the protective cap) are retracted within the sheath, and the syringe plunger is in the retracted position;

FIG. 4 is a view taken on line 4—4 of FIG. 3, showing means for locking the piston in the retracted position;

FIG. 5 is a view similar to FIG. 4, showing an alternate embodiment for locking the piston in the retracted position;

FIG. 6 is another view similar to FIG. 5, showing yet another embodiment for locking the piston in the retracted position;

FIG. 7 is a fragmentary sectional view of an alternate embodiment of the piston in the extended position in the sheath; and FIG. 8 is a fragmentary sectional view of another embodiment of the piston in the extended position in the sheath.

DESCRIPTION OF THE PREFERRED EMBODIMENTS

Referring to FIGS. 1–4, the safety device 12 includes an elongated, cylindrical sheath 14 with a cylindrical sidewall 15 open at one end 16 and partially closed at the other end 17 by an end wall 18 with a bore 20 extending longitudinally through the central area of the end wall. An outwardly extending flange 21, formed integrally with the sheath, surrounds the open end of the sheath.

A cylindrical piston 22, with an outside diameter slightly less than the inside diameter of the sheath, is mounted within the sheath to slide longitudinally between an extended position (FIG. 1) adjacent the end wall 18 and a retracted position (FIG. 3) adjacent the open end of the sheath. The piston includes a circular end wall 24 facing the inside surface of the sheath end wall 18. An annular skirt 26, formed integrally with the periphery of the piston end wall 24, extends from the open end of the sheath. The annular skirt is of sufficient length that, when the piston is in the extended position shown in FIG. 1, the end of the skirt remote from the piston projects from the open end of the sheath. An outwardly extending annular handle 27 facilitates sliding the piston to the retracted position shown in FIG. 3.

A central bore 32 extends longitudinally through the piston wall to be collinear with the bore 20 through the sheath end wall 18.

A syringe 36, which may be of conventional type, includes a hollow, elongated, cylindrical barrel 38 disposed coaxially within the sheath. A plunger 40 makes a sliding fit within the barrel so that when the plunger is moved from the retracted position shown in FIG. 3 toward the extended position shown in FIG. 1, fluid within the barrel is forced out through a central bore 42 in a tapered plug 44 at the discharge end of the syringe. As shown in FIG. 1, the tapered plug on the discharge end of the syringe forms a fitting which tapers inwardly in the direction away from the open end of the sheath. The tapered plug extends through the central bore 32 in the piston end wall and into a matching tapered socket 46 formed in a hub 48 molded around an elongated cannula 50, which has a scarf 52 at its outer end. An elongated cannula cap 54 fits over the cannula and makes a snug friction fit around the hub.

As shown in FIGS. 1 and 3, the central bore 32 through the piston end wall 24 is of smaller diameter than the barrel or the nd of the tapered plug 44 adjacent the barrel, and of smaller diameter than the outer diameter of the hub, so the piston end wall is trapped or sandwiched between the discharge end of the syringe and the end of the hub which carries the tapered socket or fitting. Thus, as the syringe barrel is moved longitudinally relative to the sheath, the piston, skirt, hub and cannula also move longitudinally with respect to the sheath.

As shown in FIGS. 1 and 3, the piston carries a laterally extending pin 60, which extends through a longitudinal slot 62 in the sidewall of the sheath, and into an exterior sleeve 61, which makes a close sliding fit around the outside of the sheath. The slot 62 extends from the closed end of the sheath and terminates adjacent the open end of the sheath.

If desired, the end of the slot 62 adjacent the closed end of the sheath may include a section 64 (see FIG. 2) of reduced width to provide a detent action for the cylindrical pin when the piston and pin are moved to the extended position shown in FIG. 1. The retaining force of the detent at section 64 is relatively slight, i.e., the diameter of the pin is only slightly greater than the width of the section 64, so the piston can be moved to the retracted position by simply sliding the syringe barrel to the right (as viewed in FIGS. 1 and 3) toward the retracted position, and without causing the tapered fittings on the barrel and cannula hub to decouple. Alternatively, the pin can be moved out of the detent or the extended position by applying force manually to the portion of the pin which projects laterally from the sidewall of the sheath. An outwardly extending annular handle 65 on the end of the sleeve nearer the open end of the sheath may also be used to slide the sleeve, pin, and piston to the retracted position by using only one hand. This is done by simply placing the thumb on the outwardly extending flange 21 at the open end of the sheath and placing the sleeve between the index and middle fingers. With the device held in this manner, and pulling the sleeve handle toward the thumb, the piston and cannula are moved to the retracted position shown in FIG. 3.

As shown in FIG. 4, the end of the slot 62 adjacent the open end of the sheath includes a narrow section 70 of reduced width substantially less than the diameter of the pin, so that when the sleeve and pin are forced down to the open end of the sheath, the pin 60 is jammed through the narrow section 70 of the slot with a force much stronger than that required with respect to the narrow section 64 at the other end of the slot. Preferably, the pin or sheath sidewall are made of plastic or other suitable material which yields sufficiently to let the pin be forced to the position shown in FIG. 4. Thus, the sleeve and piston may be substantially locked in the retracted position shown in FIGS. 3 and 4.

FIG. 5 shows an alternate embodiment in which the end of the slot at the open end of the sheath includes an L-shaped section 72, which is of slightly less width than the diameter of the pin, so that as the pin is forced toward the open end of the sheath, the L-shaped section 72 of reduced width forces the pin to travel in a circumferential direction around the longitudinal axis of the sheath, securing locking the sleeve and piston against accidental displacement from the retracted position.

FIG. 6 shows yet another embodiment of a pin 73, which in cross section looks like an arrowhead 74 pointing toward the open end of the sheath. The slot adjacent the open end of the sheath includes a pair of ramps 76, which extend inwardly in the direction of the open end of the sheath to form a ratchet past which the arrowhead-shaped portion of the pin may be forced and locked against accidental displacement in the opposite direction.

In using the safety device shown in FIGS. 1-6, the piston is moved to the extended position shown in FIG. 1, and the covered cannula and hub are removed from the tapered plug at the discharge end of the hypodermic syringe. Alternatively, the cannula and hub may be separately packaged from the syringe. In either case, the uncovered plug of the syringe is then inserted into the open end of the sheath from right to left (as viewed in FIG. 1) through the central bore 32 in the piston. The tapered socket of the cannula hub is slipped from left to right (as viewed in FIG. 1) to make a snug friction fit over the exposed end of the tapered plug on the discharge end of the hypodermic syringe. Thus, the piston is securely clamped or sandwiched between the cannula hub and the discharge end of the syringe.

The syringe is loaded by drawing medication into it so the syringe plunger is in the retracted position shown in FIG. 3. The detent action of the narrow portion 64 of the slot and the pin holds the piston in the extended position while the syringe plunger is moved to the retracted position to fill the syringe barrel with medication. The syringe barrel may also be held firmly in the extended position by hand to aid the detent action, if needed. The assembly is now ready for use by simply removing the cannula cap to expose the scarf of the cannula.

After the fluid in the syringe has been expelled by pushing the plunger from the retracted position shown in FIG. 3 to the extended position shown in FIG. 1, the needle is removed from the injecting position. This can be done by either holding the sheath in the fixed position while withdrawing the needle by moving the pin 60, or the syringe barrel 38, to the right (as shown in FIG. 3) to cause the piston 22 to slide to the retracted position shown in FIG. 3. The pin 60 is forced to any of the locked positions shown in FIGS. 4, 5, or 6, depending upon which embodiment is used.

Thus, the needle is withdrawn and sheathed at the same time. Alternatively, the needle may be withdrawn before sheathing and thereafter sliding the piston from the extended position of FIG. 1 to the retracted position of FIG. 3, where the scarf end of the cannula is completely enclosed within the sheath.

For additional safety, a plug 78 is inserted into the bore 20 in the end wall at the closed end of the sheath.

FIG. 7 shows an alternate embodiment of a piston 80 mounted to slide in the sheath 14, which has the same longitudinal slot 62 shown in FIG. 1.

A laterally extending pin 82 extends from the piston through the longitudinal slot 62.

A bore 84 extends longitudinally through the piston and tapers outwardly to the right (as viewed in FIG. 7) toward the open end of the sheath and through a longitudinally extending boss 86 projecting from the piston toward the open end of the sheath. The outer end of the boss carries a pair of outwardly extending ears 88, which form the equivalent of male threads of a conventional Luer Lock connection found on the hub of a conventional removable cannula adapted to be connected to the discharge end of a hypodermic syringe. Such a lock is shown in U.S. Pat. No. 4,737,114 to Choksi. Thus, the internally threaded socket of a Luer Lock of a conventional hypodermic syringe may be threaded onto the ears 88 to draw the tapered plug (not shown in FIG. 7) of the hypodermic syringe snugly into the tapered outlet of central bore 84 in the piston.

An internally threaded socket 90 is formed in the piston to open toward the end wall 18 of the sheath. The socket surrounds a tapered boss 92 of conventional construction similar to that of the socket/tapered boss of a conventional Luer Lock at the discharge end of a hypodermic syringe.

With the piston shown in FIG. 7, the socket on the discharge end of a hypodermic syringe with a conventional Luer Lock connection can be threaded around the ears on the boss 86 to form a fluid tight seal inside the tapered portion of the bore 84. Similarly, the outwardly extending ears on the typical Luer Lock hub (not shown in FIG. 7) mounted on a cannula can be threaded into the internally threaded socket 90 of the piston to cause the tapered boss 92 to fit snugly into the tapered socket of the hub. Thus, a fluid tight seal is effected from the hub to the boss 92 so that a fluid tight connection is made from the interior of the cannula to the interior of the syringe barrel.

FIG. 8 shows an alternate embodiment of a piston 94, which includes a centrally located socket 95 tapered outwardly in the direction of the open end of the sheath, and a plug 96, which is tapered inwardly toward the closed end of the sheath. A longitudinal bore 97 through the plug 96 connects the exterior of the plug with the interior of socket 95.

The conventional tapered plug (not shown) of a hypodermic syringe barrel fits snugly into tapered socket 95. A tapered socket (not shown) on a cannula hub (not shown) makes a snug fit over the tapered plug 96, which projects through the central bore 20 of the end wall at the closed end of the sheath. Thus, the conventional tapered fittings on the end of a conventional hypodermic syringe and cannula hub can be fitted onto the piston exactly as they are normally fitted together in prior practice.

From the foregoing description, it is clear that the safety device of this invention can be used with many different types and sizes of standard hypodermic syringes which employ removable cannulas.

I claim:

1. A protective device for a removable cannula used with a hypodermic syringe, the device comprising:

an elongated sheath open at a first end and having a longitudinally extending slot;

a hypodermic syringe barrel disposed within the sheath and having a plunger with a first end extending from a first end of the barrel and from the open end of the sheath;

a fitting at a second end of the barrel, the barrel fitting having an opening extending through it to communicate with the barrel interior;

an elongated hypodermic cannula having a longitudinal opening extending through it;

a fitting on the cannula, the fitting being constructed and arranged to mate with the barrel fitting and hold the cannula so the cannula opening communicates with the barrel interior through the opening in the barrel fitting;

a piston having a central opening and disposed in the sheath to be sandwiched between the two fittings and to be longitudinally slidable with the barrel, fittings, and cannula relative to the sheath between an extended position and a retracted position, the sheath being sufficiently long so that, when the piston is in the retracted position, the scarf end of the cannula is safely enclosed within the sheath; and a pin secured to the piston and extending laterally into the slot.

2. Apparatus according to claim 1 which includes detent means for locking the pin and piston in the extended position.

3. Apparatus according to claim 1 or 2 which includes detent means for locking the pin and piston in the retracted position.

4. Apparatus according to claim 1 which includes means for limiting travel of the piston longitudinally within the sheath.

5. Apparatus according to claim 1 or 2 which includes an end wall over the second end of the sheath, the end wall having a bore extending through it and aligned with the bore extending through the piston.

6. Apparatus according to claim 5 which includes a removable plug for closing the bore through the end wall of the sheath.

7. A protective device for a removable cannula having a fitting adapted to mate with a threaded fitting on the barrel of a hypodermic syringe, the device comprising:

an elongated sheath open at a first end;

a piston disposed in the sheath to be longitudinally slidable between an extended position and a retracted position, the piston having a longitudinal bore extending through it;

a first threaded fitting on one side of the piston and around the piston bore, the first fitting being constructed and arranged to mate with the threaded fitting on the barrel of the hypodermic syringe; and a second threaded fitting on the other side of the piston and around the piston bore, the second threaded fitting being constructed and arranged to mate with the fitting on the cannula, the sheath being sufficiently long so that when the piston is in the retracted position with the cannula fitting connected to the piston, the cannula is safely enclosed within the sheath.

8. Apparatus according to claim 7 in which the sheath has an elongated slot, and a pin is secured to the piston to extend transversely into the slot.

9. Apparatus according to claim 7 or 8 which includes detent means for locking the piston in the extended position.

10. Apparatus according to claim 9 which includes detent means for locking the piston in the retracted position.

11. Apparatus according to claim 7 which includes means for limiting the longitudinal travel of the piston in the sheath.

12. Apparatus according to claim 7 which includes an end wall for closing the second end of the sheath, the end wall having a longitudinally extending bore through it substantially collinear with the bore through the piston.

13. Apparatus according to claim 12 which includes a removable plug for closing the bore extending through the end wall at the second end of the sheath.

14. Apparatus according to claim 7 in which the first fitting on one side of the piston includes a tapered socket, and the second fitting on the other side of the piston includes a tapered plug.

* * * * *